US012805734B2

(12) United States Patent
Kuenen et al.

(10) Patent No.: US 12,805,734 B2
(45) Date of Patent: Nov. 24, 2026

(54) APPARATUS FOR USE WITH A WEARABLE CUFF

(71) Applicant: KONINKLIJKE PHILIPS N.V., Eindhoven (NL)

(72) Inventors: Maarten Petrus Joseph Kuenen, Veldhoven (NL); Paul Aelen, Eindhoven (NL); Teun Van Den Heuvel, Deventer (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 789 days.

(21) Appl. No.: 17/041,370

(22) PCT Filed: Mar. 27, 2019

(86) PCT No.: PCT/EP2019/057655
§ 371 (c)(1),
(2) Date: Sep. 24, 2020

(87) PCT Pub. No.: WO2019/185672
PCT Pub. Date: Oct. 3, 2019

(65) Prior Publication Data

US 2021/0121073 A1 Apr. 29, 2021

(30) Foreign Application Priority Data

Mar. 28, 2018 (EP) .................................... 18164614

(51) Int. Cl.
*A61B 5/022* (2006.01)
*A61B 5/00* (2006.01)
*A61B 5/021* (2006.01)

(52) U.S. Cl.
CPC .......... *A61B 5/022* (2013.01); *A61B 5/02141* (2013.01); *A61B 5/7217* (2013.01); *A61B 2560/04* (2013.01)

(58) Field of Classification Search
CPC combination set(s) only.
See application file for complete search history.

(56) References Cited

U.S. PATENT DOCUMENTS 4,263,918 A * 4/1981 Swearingen ....... A61B 5/02116 600/494
8,740,803 B2 6/2014 Hersh
(Continued)

FOREIGN PATENT DOCUMENTS

| | | | |
|---|---|---|---|
| WO | 84/01499 | A1 | 4/1984 |
| WO | 2017129495 | A1 | 8/2017 |
| WO | 2019155048 | A1 | 8/2019 |

OTHER PUBLICATIONS

Abderahman et al. An integrated blood pressure measurement system for suppression of motion artifacts Computer Methods and Programs in Biomedicine 145 (2017) 1-10 (Year: 2017).*
(Continued)

*Primary Examiner* — Jay B Shah
(74) *Attorney, Agent, or Firm* — Brynne J. Corcoran

(57) ABSTRACT

There is provided an apparatus (12) for use with a wearable cuff (14) in determining blood pressure and/or pulse rate. The wearable cuff (14) is inflatable to pressurize a measurement site of a subject (18). The apparatus (12) is configured to acquire a pressure signal indicative of pressure in the wearable cuff (14) during inflation of the wearable cuff (14) to pressurize the measurement site of the subject (18) and analyze the acquired pressure signal to detect an artifact corresponding to a decrease in pressure during inflation of the wearable cuff (14) due to cuff slippage. The apparatus (12) is also configured to determine the blood pressure and/or pulse rate of the subject (18) by analyzing oscillations in the acquired pressure signal, wherein determining comprises compensating for the detected artifact.

20 Claims, 7 Drawing Sheets

(56) References Cited

U.S. PATENT DOCUMENTS

| | | | | |
|---|---|---|---|---|
| 2004/0059234 | A1* | 3/2004 | Martin et al. | A61B 5/024 600/500 |
| 2008/0234589 | A1* | 9/2008 | Riobo Aboy | A61B 5/0225 600/490 |
| 2009/0209868 | A1* | 8/2009 | Hersh et al. | A61B 5/0225 600/485 |
| 2010/0114209 | A1* | 5/2010 | Krause | A61N 1/37217 607/32 |
| 2011/0152698 | A1* | 6/2011 | Greenhut | A61B 5/0215 600/486 |
| 2012/0046561 | A1 | 2/2012 | Usuda | |
| 2012/0245478 | A1* | 9/2012 | Whitaker et al. | A61B 5/7203 600/499 |
| 2013/0060152 | A1 | 3/2013 | Baron | |
| 2015/0073284 | A1 | 3/2015 | Welch | |
| 2015/0137988 | A1 | 5/2015 | Gravenstein | |
| 2018/0235488 | A1 | 8/2018 | Aelen | |

OTHER PUBLICATIONS

International Search Report and Written Opinion of PCT/EP2019/057655, dated Jun. 26, 2019.

* cited by examiner

APPARATUS FOR USE WITH A WEARABLE CUFF

This application is the U.S. National Phase application under 35 U.S.C. § 371 of International Application No. PCT/EP2019/057655, filed on Mar. 27, 2019, which claims the benefit of European Application Serial No. 18164614.2, filed Mar. 28, 2018. These applications are hereby incorporated by reference herein.

FIELD OF THE INVENTION

The idea relates to an apparatus and a method of operating the apparatus for use with a wearable cuff in determining blood pressure and/or pulse rate.

BACKGROUND OF THE INVENTION

Blood pressure (BP) or, more precisely, arterial blood pressure, is the pressure exerted by circulating blood on the arterial vessel walls. It is one of the key vital signs to establish patient well-being and therefore needs to be monitored for patients at risk. Blood pressure is a periodic signal, which rises at each contraction of the heart and decreases in between heart beats. It is typically described by systolic blood pressure (SBP), diastolic blood pressure (DBP) and mean arterial blood pressure (MAP), where systolic blood pressure is the maximum blood pressure during heart cycle, diastolic blood pressure is the minimum blood pressure during heart cycle, and mean arterial blood pressure is the average blood pressure during a heart cycle.

Different techniques exist by which blood pressure can be determined and these can be classified as invasive or non-invasive measurement techniques. Typically, non-invasive measurement techniques are cuff-based, which require an inflatable cuff to be placed around a limb (which is usually the upper arm) of a subject. The pressure in the cuff is then changed to infer blood pressure. There are two common methods that use a cuff in this way, which are referred to in the art as the auscultatory method and the oscillometric method respectively.

The auscultatory method for blood pressure measurement is based on the appearance and disappearance of sounds created by the artery under the cuff during the period that the cuff pressure is changed. These sounds are referred to in the art as Korotkoff sounds. The pressures at which the Korotkoff sounds appear and vanish are indicative of DBP and SBP with Korotkoff sounds appearing at each heart beat between DBP and SBP. The measurement of sound can be performed manually with a stethoscope that is placed over the artery just below the cuff, or in an automated way with a microphone under the cuff.

In the oscillometric method for blood pressure measurement, the systolic and diastolic blood pressure values are based on small volume oscillations or pressure oscillations that are induced in the cuff by each heart beat. The amplitude of these volume or pressure oscillations depends on the difference between the cuff pressure and the actual arterial blood pressure. Systolic blood pressure and diastolic blood pressure are then determined as the cuff pressure where the volume or pressure oscillations have amplitudes of a certain fraction of the maximum oscillation amplitude. These fractions are typically heuristically determined.

In both the auscultatory and oscillometric method, the mean arterial pressure is typically calculated as: $MAP=\frac{2}{3}*DBP+\frac{1}{3}*SBP$.

The oscillometric and auscultatory measurement methods can be performed either during inflation of the cuff or during deflation of the cuff. Conventionally, measurements during deflation are used, in which the cuff is rapidly inflated to a level above the SBP where the blood flow in the artery under the cuff is blocked, after which cuff pressure is decreased gradually or in a stepwise manner. During deflation, the volume or pressure oscillations or the Korotkoff sounds are measured. While deflation stage measurement is well-established, an issue exists in the discomfort it introduces to the subject. In particular, the subject is exposed to a relatively high cuff pressure for a certain amount of time and pressures above a certain level can be uncomfortable and even painful, either due to the pressure exerted by the cuff itself or due to a build-up of venous blood in the clamped extremity (namely, venous pooling). The longer these pressures are applied to the subject, the higher the discomfort level is for the subject.

Another issue with utilizing the deflation based blood pressure measurement is that the process of inflating the cuff and then deflating the cuff can be considerably long, where each measurement during deflation typically takes 40 seconds to complete. Also, since a defined maximum pressure level needs to be achieved before the deflation procedure can be initiated, the subject is exposed to a maximum cuff pressure that is higher than that required for the blood pressure measurement itself. Furthermore, the inherent variability of blood pressure over time can distort a single blood pressure measurement.

Due to these issues, devices have been developed that determine oscillations during inflation of the blood pressure cuff. These devices can reduce the discomfort as blood pressure measurement may be accomplished in less time using the inflation stage, rather than the deflation stage. In order to have the measurement time as short as possible without sacrificing accuracy, the cuff inflation speed can be made pulse rate dependent such that the optimal number of oscillations (i.e. enough to assure a certain accuracy but no more) is present for determining blood pressure. Thus, once the pressure range of interest is achieved at the inflation stage, pressure relief may be initiated so as to reduce the overall measurement time and the pressure-based discomfort.

However, in general, non-invasive blood pressure (NIBP) measurements are easily distorted due to the small amplitude of the pressure oscillations. One such distortion relates to the sudden recuperation of volume that often occurs during inflation of the blood pressure cuff. The recuperation of volume is an effect that is related to the blood pressure cuff (gradually) becoming pressurized during inflation.

During this pressurization, the material that holds the cuff around the arm needs to generate a higher counter force per area. Although this prevents the cuff from falling off during a measurement, the cuff may not be secured tight enough at local parts and may come loose. For example, the fastening (e.g. Velcro) that holds the cuff in place may detach during inflation. When this happens, the volume of the cuff expands locally. This produces a characteristic sound. Also, during pressurization of the cuff, the bladder of the cuff (which is usually a plastic or rubber like material) expands. At the initiation of a blood pressure measurement, the bladder of the cuff can comprise small folds that result in parts of the bladder volume being closed off. During inflation, the bladder expands and this can result in the unfolding of the folds, which also produces a recuperation of volume.

These effects can result in cuff slippage, which introduces an artifact in the pressure signal acquired from the wearable cuff. As such, the existing inflation based techniques that measure blood pressure from this pressure signal, can lead to inaccurate (e.g. false) or even unsuccessful blood pressure measurements. In the worst case, the inaccurate or unsuccessful blood measurements can result in a medical professional (e.g. a physician or nurse) making an incorrect diagnosis or initiating the wrong action. U.S. Pat. No. 8,911,378 discloses a method for determining that a cuff slippage condition exists. However, even in this method, inaccurate blood measurements occur since the cuff slippage condition is simply ignored if it is not severe or unsuccessful blood measurements occur since the measurement of blood pressure is otherwise terminated on detection of the cuff slippage condition.

SUMMARY OF THE INVENTION

As noted above, a limitation with existing techniques for measuring blood pressure during inflation of a wearable cuff is that cuff slippage can occur during inflation, which causes inaccurate or even unsuccessful blood pressure measurements. It would thus be valuable to address the limitations with existing techniques.

Therefore, according to a first aspect, there is provided an apparatus for use with a wearable cuff in determining blood pressure and/or pulse rate. The wearable cuff is inflatable to pressurize a measurement site of a subject. The apparatus is configured to acquire a pressure signal indicative of pressure in the wearable cuff during inflation of the wearable cuff to pressurize the measurement site of the subject, analyze the acquired pressure signal to detect an artifact corresponding to a decrease in pressure during inflation of the wearable cuff due to cuff slippage, and determine the blood pressure and/or pulse rate of the subject by analyzing oscillations in the acquired pressure signal, wherein determining comprises compensating for the detected artifact.

In some embodiments, the apparatus may be configured to analyze the acquired pressure signal by analyzing raw data of the acquired pressure signal to detect the artifact. In some embodiments, the apparatus may be configured to analyze the acquired pressure signal by taking a derivative of the acquired pressure signal and analyzing the derivative of the acquired pressure signal to detect the artifact.

In some embodiments, the apparatus may be configured to compensate for the detected artifact by any one or more of discarding oscillations in the acquired pressure signal at one or more occasions where the detected artifact occurs and applying a correction to the acquired pressure signal at one or more occasions where the detected artifact occurs. In some embodiments, the apparatus may be configured to apply the correction to the acquired pressure signal by subtracting the detected artifact from the raw data of the acquired pressure signal at one or more occasions where the detected artifact occurs to acquire a corrected pressure signal. In some embodiments, the apparatus may be configured to apply the correction to the acquired pressure signal by subtracting the detected artifact from the derivative of the acquired pressure signal at one or more occasions where the detected artifact occurs and integrating the derivative of the acquired pressure signal with the detected artifact subtracted to acquire a corrected pressure signal.

In some embodiments, the apparatus may be configured to detect an artifact corresponding to a decrease in pressure during inflation of the wearable cuff due to cuff slippage where the decrease in pressure is greater than a threshold decrease in pressure and/or a decrease in pressure rate is greater than a threshold decrease in pressure rate. In some embodiments, any one or more of the threshold decrease in pressure and the threshold rate of decrease in pressure rate may be adaptable. In some embodiments, the apparatus may be configured to analyze the acquired pressure signal to acquire information on amplitude. In these embodiments, any one or more of the threshold decrease in pressure and the threshold rate of pressure decrease may be adaptable based on the information acquired on the amplitude.

In some embodiments, the apparatus may be further configured to analyze the acquired pressure signal to determine a trend in pressure and prior to detecting the artifact, compensate for the determined trend in pressure such that the determined trend in pressure is omitted from the analysis of the acquired pressure signal to detect the artifact.

In some embodiments, the apparatus may be further configured to analyze the acquired pressure signal to detect one or more artifacts due to a pump operable to inflate the wearable cuff. In these embodiments, determining may further comprise compensating for the one or more detected artifacts due to the pump prior to compensating for the artifact due to cuff slippage. In some embodiments, the apparatus may be configured to determine a rotation speed of a motor of the pump operable to inflate the wearable cuff. In some of these embodiments, compensating for the one or more detected artifacts due to the pump may be based on the determined rotation speed of the motor of the pump. In some embodiments, the compensating for the one or more detected artifacts due to the pump based on the determined rotation speed of the motor of the pump may comprises suppressing one or more harmonics corresponding to the determined rotation speed of the motor of the pump.

According to a second aspect, there is provided a method of operating an apparatus for use with a wearable cuff in determining blood pressure and/or pulse rate. The wearable cuff is inflatable to pressurize a measurement site of a subject. The method comprises acquiring a pressure signal indicative of pressure in the wearable cuff during inflation of the wearable cuff to pressurize a measurement site of a subject, analyzing the acquired pressure signal to detect an artifact corresponding to a decrease in pressure during inflation of the wearable cuff due to cuff slippage, and determining the blood pressure and/or pulse rate of the subject by analyzing oscillations in the acquired pressure signal, wherein determining comprises compensating for the detected artifact.

According to a third aspect, there is provided a computer program product comprising a computer readable medium, the computer readable medium having computer readable code embodied therein, the computer readable code being configured such that, on execution by a suitable computer or processor, the computer or processor is caused to perform the method described above.

According to the aspects and embodiments described above, the limitations of existing techniques are addressed. In particular, the above-described aspects and embodiments enable the detection of an artifact due to cuff slippage in a pressure signal indicative of pressure in a wearable cuff during inflation and compensates for that artifact. Thus, artifacts due to cuff slippage are prevented from affecting blood pressure measurement and/or pulse rate measurement according to the above-described aspects and embodiments. In effect, the blood pressure measurements are insensitive to artifacts that may otherwise occur during the measurement. As such, the above-described aspects and embodiments enable a wearable cuff to be used in acquiring more accurate blood pressure measurements and/or pulse rate measurements during inflation of the wearable cuff. A more robust technique is provided for determining blood pressure and/or pulse rate by reducing or even preventing errors in measurements that result from artifacts. The limitations associated with the existing techniques discussed earlier are therefore addressed by way of the above-described aspects and embodiments.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
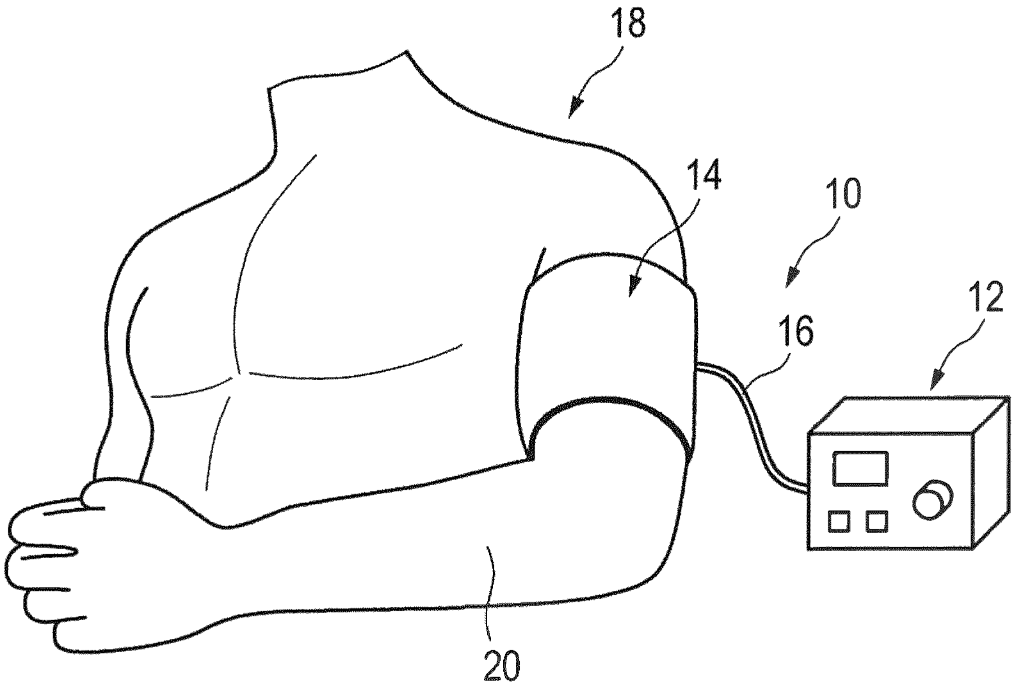
FIG. 1 is a simplified schematic illustration of an apparatus in use with a wearable cuff according to an example embodiment.

There is provided herein an apparatus for use with a wearable cuff (or clamp unit) in determining (or measuring) blood pressure and/or pulse rate, which overcomes the limitations with existing techniques. The wearable cuff referred to herein is inflatable to pressurize a measurement site of a subject (e.g. a patient). In this way, the wearable cuff can pressurize an artery in the measurement site of the subject. Typically, the wearable cuff can be supplied with a fluid (e.g. a gas, such as air, or any other fluid) suitable for inflating the wearable cuff. The wearable cuff can be inflatable to pressurize the measurement site of a subject (and thus an artery in the measurement site of the subject) at the pressure of the fluid in the wearable cuff.

The wearable cuff is configured to be worn on or around (e.g. wrapped around, attached to, or fastened to) the measurement site of the subject. The measurement site of the subject can be any site on the body of the subject that is suitable for use in measuring a blood pressure of the subject, such as any site on the body of the subject that comprises an artery. For example, the measurement site of the subject may be located on a limb of the subject, such as an arm (e.g. an upper arm or a forearm) of the subject. Thus, the wearable cuff can be configured to be worn on or around (e.g. wrapped around, attached to, or fastened to) a limb of the subject.

Briefly, the apparatus is configured to acquire a pressure signal indicative of pressure in the wearable cuff during inflation of the wearable cuff to pressurize the measurement site of the subject and analyze the acquired pressure signal to detect an artifact corresponding to a decrease in pressure during inflation of the wearable cuff due to cuff slippage. The apparatus is also configured to determine the blood pressure and/or pulse rate of the subject by analyzing oscillations in the acquired pressure signal, wherein determining comprises compensating for the detected artifact.

The detected artifact that is referred to herein can be any artifact that is characteristic of an artifact due to cuff slippage during inflation of the wearable cuff. For example, the detected artifact may be an artifact that is characteristic of an artifact due to a loosening of the wearable cuff during inflation of the wearable cuff, or an artifact that is characteristic of an artifact due to an unfolding of a fold in the wearable cuff during inflation of the wearable cuff.

As the apparatus described herein is configured to determine the blood pressure and/or pulse rate of the subject by analyzing oscillations in a pressure signal that is acquired during inflation (or at the inflation stage) of the wearable cuff, the apparatus described herein is for use in inflation-based blood pressure measurements and/or inflation-based pulse rate measurements. More specifically, the apparatus described herein is for use in inflation-based non-invasive blood pressure (iNIBP) measurements and inflation-based non-invasive pulse rate measurements. In some embodiments, the acquired pressure signal referred to herein may be in a frequency range that corresponds to a heart rate range of 30 beats/min to 300 beats/min. For example, the acquired pressure signal referred to herein may be in a frequency range from 0.5 Hz to 5 Hz according to some embodiments.

The apparatus described herein can be implemented in numerous ways, with software and/or hardware, to perform the various functions described herein. In some embodiments, the apparatus can comprise a plurality of software and/or hardware components (or modules), each configured to perform, or that are for performing, individual or multiple steps of the method described herein. For example, the apparatus may comprise one or more processors (e.g. one or more microprocessors, one or more multi-core processors and/or one or more digital signal processors (DSPs)), one or more processing units, one or more controllers (e.g. one or more microcontrollers) and/or electronics (e.g. electronic circuitry, one or more field-programmable gate arrays (FPGAs), and/or any other electronics) that may be configured or programmed (e.g. using software or computer program code) to perform the various functions described herein. The apparatus may be implemented as a combination of dedicated hardware (e.g. amplifiers, pre-amplifiers, analog-to-digital convertors (ADCs) and/or digital-to-analog convertors (DACs)) to perform some functions and one or more processors (e.g. one or more programmed processors and associated circuitry) to perform other functions.

FIG. 1 illustrates the apparatus 12 in use with a wearable cuff 14 for use in determining (or measuring) blood pressure and/or pulse rate, according to an example embodiment. There is thus provided a system 10 comprising the apparatus 12 and the wearable cuff 14. As mentioned earlier, the wearable cuff 14 is inflatable to pressurize the measurement site 20 of the subject 18. In the example embodiment illustrated in FIG. 1, the measurement site 20 of the subject 18 is located on the upper arm of the subject 18. Thus, the wearable cuff 14 is worn on or around (e.g. wrapped around, attached to, or fastened to) the upper arm of the subject 18 in this illustrated example embodiment.

As illustrated in FIG. 1, in some embodiments, the cuff 14 may be coupled with or connected to the apparatus 12 via at least one supply line (or at least one supply tube) 16, which may also be referred to as at least one pressure supply line (or at least one pressure supply tube) 16. The at least one supply line 16 can be arranged for pressurizing the wearable cuff 14 and, consequently, the measurement site 20 of the subject 18. The at least one supply line 16 may be provided for inflating and/or deflating the wearable cuff 14. As mentioned earlier, the wearable cuff 14 can be supplied with any fluid suitable for inflating the wearable cuff 14.

Although not illustrated in FIG. 1, in some embodiments, the system 10 may comprise a pump. The pump can be controllable to inflate the wearable cuff 14 in the manner described herein. In some embodiments, the apparatus 12 described herein may comprise the pump. Alternatively or in addition, a pump may be external to (e.g. separate to or remote from) the apparatus 12. A pump can thus be any pump that is controllable to inflate the wearable cuff 14. In some embodiments, the pump can be controllable by a controller of the apparatus 12 to inflate the wearable cuff 14 in the manner described herein. The controller of the apparatus 12 may communicate with and/or connect to the pump in any suitable way to control the pump.

Although also not illustrated in FIG. 1, in some embodiments, the system 10 may comprise a deflation valve. The deflation valve can be controllable to deflate the wearable cuff 14. In some embodiments, the apparatus 12 described herein may comprise the deflation valve. Alternatively or in addition, a deflation valve may be external to (e.g. separate to or remote from) the apparatus 12. A deflation valve can thus be any valve that is controllable to deflate the wearable cuff 14. In some embodiments, the deflation valve can be controllable by the controller of the apparatus 12 to deflate the wearable cuff 14. The controller of the apparatus 12 may communicate with and/or connect to the deflation valve in any suitable way to control the deflation valve.

Although also not illustrated in FIG. 1, in some embodiments, the system 10 may comprise at least one pressure sensor. The at least one pressure sensor can be configured to measure the pressure in the wearable cuff 14. In some embodiments, the apparatus 12 described herein may comprise the at least one pressure sensor configured to measure the pressure in the wearable cuff 14. Alternatively or in addition, at least one pressure sensor external to (e.g. separate to or remote from) the apparatus 12 may be configured to measure the pressure in the wearable cuff 14. For example, in some embodiments, the wearable cuff 14 itself may comprise at least one pressure sensor configured to measure the pressure in the wearable cuff 14. In some embodiments, the at least one pressure sensor can be controllable by the controller of the apparatus 12 to measure the pressure in the wearable cuff 14. The controller of the apparatus 12 may communicate with and/or connect to the at least one pressure sensor in any suitable way to control the at least one pressure sensor.

Although also not illustrated in FIG. 1, in some embodiments, the system 10 may comprise a communications interface (or communications circuitry). In some embodiments, the apparatus 12 described herein may comprise a communications interface. Alternatively or in addition, the communications interface may be external to (e.g. separate to or remote from) the apparatus 12. The communications interface can be for enabling the apparatus 12, or components of the apparatus 12, to communicate with and/or connect to one or more other components, sensors, interfaces, devices, or memories (such as any of those described herein). For example, the communications interface can be for enabling the controller of the apparatus 12 to communicate with and/or connect to any one or more of the pump, the deflation valve, and the at least one pressure sensor described earlier. The communications interface may enable the apparatus 12, or components of the apparatus 12, to communicate and/or connect in any suitable way. For example, the communications interface may enable the apparatus 12, or components of the apparatus 12, to communicate and/or connect wirelessly, via a wired connection, or via any other communication (or data transfer) mechanism. In some wireless embodiments, for example, the communications interface may enable the apparatus 12, or components of the apparatus 12, to use radio frequency (RF), Bluetooth, or any other wireless communication technology to communicate and/or connect.

Although also not illustrated in FIG. 1, in some embodiments, the system 10 may comprise a memory. In some embodiments, the apparatus 12 described herein may comprise the memory. Alternatively or in addition, the memory may be external to (e.g. separate to or remote from) the apparatus 12. The controller of the apparatus 12 may be configured to communicate with and/or connect to the memory. The memory may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, the memory can be configured to store program code that can be executed by a processor to cause the apparatus 12 to operate in the manner described herein.

Alternatively or in addition, in some embodiments, the memory can be configured to store information required by or resulting from the method described herein. For example, in some embodiments, the memory may be configured to store any one or more of the acquired pressure signal, the detected artifact, the determined blood pressure and/or pulse rate of the subject, or any other information, or any combination of information, required by or resulting from the method described herein. In some embodiments, the controller of the apparatus 12 can be configured to control the memory to store information required by or resulting from the method described herein.

Although also not illustrated in FIG. 1, the system 10 may comprise a user interface. In some embodiments, the apparatus 12 described herein may comprise the user interface. Alternatively or in addition, the user interface may be external to (e.g. separate to or remote from) the apparatus 12. The controller of the apparatus 12 may be configured to communicate with and/or connect to a user interface. The user interface can be configured to render (or output, display, or provide) information required by or resulting from the method described herein. For example, in some embodiments, the user interface may be configured to render (or output, display, or provide) one or more of the acquired pressure signal, the detected artifact, the determined blood pressure and/or pulse rate of the subject, or any other information, or any combination of information, required by or resulting from the method described herein. Alternatively or in addition, the user interface can be configured to receive a user input. For example, the user interface may allow a user to manually enter information or instructions, interact with and/or control the apparatus 12. Thus, the user interface may be any user interface that enables the rendering (or outputting, displaying, or providing) of information and, alternatively or in addition, enables a user to provide a user input. In some embodiments, the controller of the apparatus 12 can be configured to control the user interface to operate in the manner described herein.

For example, the user interface may comprise one or more switches, one or more buttons, a keypad, a keyboard, a mouse, a touch screen or an application (for example, on a smart device such as a tablet, a smartphone, or any other smart device), a display or display screen, a graphical user interface (GUI) such as a touch screen, or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces. In some embodiments, the user interface that is controlled to render information may be the same user interface as that which enables the user to provide a user input.

Although also not illustrated in FIG. 1, the apparatus 12 may comprise a battery or other power supply for powering the apparatus 12 or means for connecting the apparatus 12 to a mains power supply. It will also be understood that the apparatus 12 may comprise any other component to those described herein or any combination of components.

Figure 2:
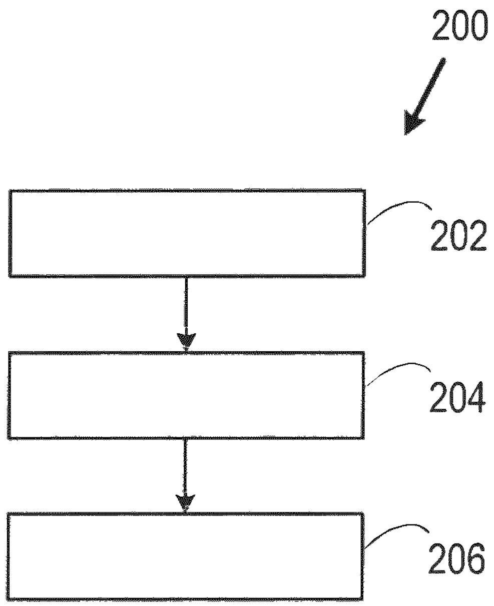
FIG. 2 is a flow chart illustrating a method of operating the apparatus according to an embodiment.

FIG. 2 illustrates a method 200 of operating the apparatus 12 described earlier for use with a wearable cuff 14 in determining blood pressure and/or pulse rate according to an embodiment. As mentioned earlier, the wearable cuff 14 is inflatable to pressurize a measurement site 20 of a subject 18. The method 200 can generally be performed by or under the control of the apparatus 12 (or any one or more of the software and/or hardware components mentioned earlier). At block 202 of FIG. 2, a pressure signal indicative of pressure in the wearable cuff 14 is acquired during inflation of the wearable cuff 14 to pressurize a measurement site 20 of a subject 18.

At block 204 of FIG. 2, the acquired pressure signal is analyzed to detect an artifact corresponding to a decrease in pressure during inflation of the wearable cuff 14 due to cuff slippage. Thus, the apparatus 12 is configured to detect artifacts due to cuff slippage based on cuff pressure. The detected artifact referred to herein is an artifact that distorts the acquired pressure signal. For example, during the inflation process of a wearable cuff 14, the oscillation in the acquired pressure signal may be distorted due to artifacts that occur as the wearable cuff 14 is being pressurized. The extent of artifacts may depend on one or more factors. Examples of such factors include, but are not limited to the pressure in the wearable cuff 14, the type of wearable cuff 14, the manner in which the wearable cuff 14 is worn on or around (e.g. wrapped around, attached to, or fastened to) the measurement site 20 of the subject 18, an area of a fastening (e.g. Velcro) that holds or fixes the wearable cuff 14 in place at the measurement site 20 of the subject 18 (which can, for example, depend on the size of the wearable cuff 14 and/or a diameter of the measurement site 20, e.g. a limb, of the subject 18), or any other factors, or any combination of factors, that can affect the extent of artifacts.

In some embodiments, the apparatus 12 may be configured to analyze the acquired pressure signal by analyzing raw data of the acquired pressure signal to detect the artifact. Herein, the raw data of the acquired pressure signal is defined as a variation with time of the pressure directly measured by the apparatus 12 during the cuff inflation. In other embodiments, the apparatus 12 may be configured to analyze the acquired pressure signal by taking a derivative (e.g. a time derivative d/dt) of the acquired pressure signal and analyzing the derivative of the acquired pressure signal to detect the artifact. Thus, the detected artifact can be compensated in either the pressure domain or the pressure rate domain. In any of the embodiments described herein involving the derivative of the acquired pressure signal, the apparatus 12 can be configured to take the derivative of the acquired pressure signal by filtering the raw data of the acquired pressure signal (e.g. using a difference filter, or any other filter suitable for taking the derivative of the acquired pressure signal). The derivative of the acquired pressure signal may also be referred to as the pressure rate signal.

As mentioned earlier, the detected artifact due to cuff slippage corresponds to a decrease in pressure during inflation of the wearable cuff 14. This decrease in pressure during inflation of the wearable cuff 14 is the result of an increase in volume during inflation of the wearable cuff 14. This is the effect of a volume recuperation during inflation of the wearable cuff 14 and this can be explained by Boyle's law, which states that the product of pressure and volume remains constant. The decrease in pressure during inflation of the wearable cuff 14 can be detected as a negative step that is superimposed on the raw data of the acquired pressure signal or a negative impulse that is superimposed on the derivative (e.g. a time derivative d/dt) of the acquired pressure signal, i.e. on the pressure rate signal.

In some embodiments, the apparatus 12 may be configured to detect an artifact corresponding to a decrease in pressure during inflation of the wearable cuff 14 due to cuff slippage using a filter (e.g. a matched filter) on the raw data of the acquired pressure signal and/or on the derivative of the acquired pressure signal, i.e. the pressure rate signal. In the embodiment using a matched filter, the filter coefficients can be configured to correspond to the reverse of a typical artifact signal due to cuff slippage. Alternatively, different filtering approaches (including, but not limited to high-pass filters and regression filtering) may be used to subtract the longer term trend in either the raw data of the acquired pressure signal and/or the pressure rate signal prior to artifact detection. Alternatively or subsequently to using a filter, in some embodiments, the apparatus 12 may be configured to detect an artifact corresponding to a decrease in pressure during inflation of the wearable cuff 14 due to cuff slippage using a threshold. Alternatively, machine learning (e.g. Bayesian learning or deep learning) approaches may be used for artifact detection.

For example, in some embodiments, the apparatus 12 may be configured to detect an artifact corresponding to a decrease in pressure during inflation of the wearable cuff due to cuff slippage where the decrease in pressure is greater than a threshold decrease in pressure and/or a decrease in pressure rate that is greater than a threshold decrease in pressure rate. In some of these embodiments, one or more of the threshold decrease in pressure and the threshold decrease in pressure rate can be adaptable. In some embodiments, for example, the threshold decrease in pressure can depend on the raw data of the acquired pressure signal itself. Similarly, in some embodiments, the threshold decrease in pressure rate can depend on the pressure rate signal itself. In this way, the compensation of artifacts due to cuff slippage can be prevented from interfering with the detection of oscillations in the acquired pressure signal. For example, an oscillation is always seen as an increase in pressure, followed by a gradual decrease in pressure, whereas a sudden volume recuperation due to cuff slippage leads to a more rapid decrease in the pressure. Thus, by way of a threshold that is adaptable based on the signal itself, artifacts due to cuff slippage are only detected when they can be clearly distinguished from actual oscillations, thereby preventing misclassification of an oscillation as an artifact due to cuff slippage and ensuring the compensation of artifacts due to cuff slippage does not interfere with the oscillations in the acquired pressure signal.

In some embodiments involving an adaptive threshold, the apparatus 12 can be configured to analyze the acquired pressure signal to acquire information on amplitude and then any one or more of the threshold decrease in pressure and the threshold rate of pressure decrease may be adaptable based on the information acquired on the amplitude. In some embodiments, the apparatus 12 may be configured to analyze the acquired pressure signal by analyzing the raw data of the acquired pressure signal to acquire information on amplitude. In other embodiments, the apparatus 12 may be configured to analyze the acquired pressure signal by taking a derivative (e.g. a time derivative d/dt) of the acquired pressure signal and analyzing the derivative of the acquired pressure signal to acquire information on amplitude.

The threshold decrease in pressure and/or the threshold decrease in pressure rate may also be referred to as an artifact detection threshold. In some embodiments, for example, the threshold decrease in pressure and/or the threshold decrease in pressure rate may be determined by a running maximum of the acquired pressure signal over a predefined time period (e.g. a time period of 0.25 seconds). In some embodiments, the threshold decrease in pressure and/or the threshold decrease in pressure rate may be set to a predefined value times the running maximum. The threshold decrease in pressure and/or the threshold decrease in pressure rate can thus be a dynamic threshold. If the raw data of the acquired pressure signal becomes lower than the threshold decrease in pressure or if the derivative of the acquired pressure signal becomes lower than the threshold decrease in pressure rate, an artifact is detected.

In some embodiments, the decrease in pressure during inflation of the wearable cuff due to cuff slippage may be a decrease in pressure that is learned by the apparatus 12 over time. For example, in some embodiments, the apparatus 12 can be configured to learn the decrease in pressure to detect during inflation of the wearable cuff due to cuff slippage through machine learning (e.g. Bayesian classification, deep learning, or any other machine learning technique, or any combination of machine learning techniques). For example, in this way, the apparatus 12 can be configured to classify a decrease in pressure during inflation of the wearable cuff as a decrease in pressure due to cuff slippage. The decrease in pressure during inflation of the wearable cuff due to cuff slippage may be learned by the apparatus 12 over time from the raw data of the acquired pressure signal (i.e. in the pressure domain) or from the derivative of the acquired pressure signal (i.e. in the pressure rate domain). Similarly, the apparatus 12 can be configured to classify a decrease in pressure during inflation of the wearable cuff as a decrease in pressure due to cuff slippage in the pressure domain and/or the pressure rate domain.

Returning back to FIG. 2, at block 206, the blood pressure and/or pulse rate of the subject is determined by analyzing oscillations in the acquired pressure signal. The detection of the artifact can be performed prior to analysis of the oscillations in the acquired pressure signal to determine the blood pressure and/or pulse rate of the subject. As mentioned earlier, the determination of the blood pressure and/or pulse rate of the subject comprises compensating for the detected artifact. In the raw data of the acquired pressure signal, the detected artifact is a negative step and can thus be compensated by compensating for the negative step in the raw data of the acquired pressure signal. Equivalently, in the pressure rate signal, the detected artifact is a negative impulse in the pressure rate signal and can thus be compensated by compensating for the negative impulse in the pressure rate signal.

In some embodiments, the apparatus 12 can be configured to compensate for the detected artifact by discarding oscillations in the acquired pressure signal at one or more occasions where the detected artifact occurs (e.g. to prevent the detected artifact causing errors in the determined blood pressure and/or pulse rate). Thus, in effect, the apparatus 12 can be configured to discard the acquired pressure signal at occasions where it is distorted by the detected artifact. In this way, the artifact is prevented from affecting the determined blood pressure and/or pulse rate. In some embodiments, a size of the part of the acquired pressure signal that is discarded may be based on a response of a filter (e.g. a step response of a bandpass filter) that is used for oscillation detection.

Alternatively or in addition, in some embodiments, the apparatus 12 can be configured to compensate for the detected artifact by applying a correction to the acquired pressure signal at one or more occasions where the detected artifact occurs (e.g. to suppress or even remove or eliminate the detected artifact in the acquired pressure signal). Thus, in effect, the apparatus 12 can be configured to correct the effect of cuff slippage on the acquired pressure signal. In this way, the artifact is prevented from affecting the determined blood pressure and/or pulse rate. In some embodiments, the correction to apply to the acquired pressure signal can be a correction signal.

The correction may be determined in the pressure domain (e.g. from the raw data of the acquired pressure signal) or in the pressure rate domain (e.g. from the derivative of the acquired pressure signal). In the pressure domain, the correction may be determined as an inverse of the artifact detected in the raw data of the acquired pressure signal. In the pressure rate domain, the correction may be determined as an inverse of the artifact detected in the derivative of the acquired pressure signal. In some embodiments where the correction is determined in the pressure domain, the correction may be applied directly to the raw data of the acquired pressure signal. In some embodiments where the correction is determined in the pressure rate domain, the correction may either be applied to (e.g. subtracted from) the derivative of the acquired pressure signal directly, or integrated to acquire a correction in the pressure domain and then be applied to (e.g. subtracted from) the raw data of the acquired pressure signal.

In some embodiments, where the correction is applied to the raw data of the acquired pressure signal, the apparatus 12 can be configured to apply the correction to the acquired pressure signal by subtracting the detected artifact from the raw data of the acquired pressure signal at one or more occasions (e.g. events) where the detected artifact occurs to acquire a corrected pressure signal. The subtraction of the detected artifact from the raw data of the acquired pressure signal can, for example, comprise adding an inverse of the detected artifact to the raw data of the acquired pressure signal. In embodiments, where the correction is applied to the derivative of the acquired pressure signal, the apparatus 12 can be configured to apply the correction to the acquired pressure signal by subtracting the detected artifact from the derivative of the acquired pressure signal (i.e. from the pressure rate signal) at one or more occasions where the detected artifact occurs and integrating the derivative of the acquired pressure signal with the detected artifact subtracted to acquire a corrected pressure signal. The subtraction of the detected artifact from the derivative of the acquired pressure signal can, for example, comprise adding an inverse of the detected artifact to the derivative of the acquired pressure signal. In some embodiments, the compensation of the detected artifact due to cuff slippage may take into account an onset of the detected artifact due to cuff slippage. For example, cuff slippage can take a certain time to reach its minimum rate. Thus, in some embodiments, the artifact due to cuff slippage may be compensated in the manner described herein on expiry of an estimated time for cuff slippage to reach its maximum rate. Although this may result in the signal to which the compensation is applied being delayed, the delay is only short and thus the compensation of the detected artifact can be performed in (near) real-time.

In some embodiments, the apparatus 12 can be configured to perform the method or parts of the method described with reference to FIG. 2 in real-time. For example, in some embodiments, the apparatus 12 can be configured to perform the method described with reference to blocks 202, 204 and 206 of FIG. 2 in sequence or at least in part simultaneously or concurrently.

Although not illustrated in FIG. 2, in some embodiments, the apparatus 12 can be further configured to analyze the acquired pressure signal to determine a trend in pressure. The trend in pressure can, for example, be representative of a baseline pressure. In some embodiments, the trend in pressure may be an average of the acquired pressure signal, such as a moving average of the acquired pressure signal over a predefined time period (e.g. over 1 second). In some embodiments where the trend in pressure is determined, prior to detecting the artifact due to cuff slippage (at block 204 of FIG. 2), the apparatus 12 can be configured to compensate for the determined trend in pressure such that the determined trend in pressure is omitted (or removed) from the analysis of the acquired pressure signal to detect the artifact.

The determined trend in pressure can be compensated in either the pressure domain or the pressure rate domain. In the pressure domain, for example, the apparatus 12 may be configured to analyze the acquired pressure signal by analyzing the raw data of the acquired pressure signal to determine the trend in pressure. In some of these embodiments, the apparatus 12 can be configured to compensate for the determined trend in pressure by subtracting the determined trend in pressure from the raw data of the acquired pressure signal. In some embodiments, the subtraction of the determined trend in pressure from the raw data of the acquired pressure signal may comprise a linear subtraction of the determined trend in pressure from the raw data of the acquired pressure signal. In the pressure rate domain, for example, the apparatus 12 may be configured to analyze the acquired pressure signal by taking a derivative (e.g. a time derivative d/dt) of the acquired pressure signal and analyzing the derivative of the acquired pressure signal to determine the trend in pressure. In some of these embodiments, the apparatus 12 can be configured to compensate for the determined trend in pressure by subtracting the determined trend in pressure from the derivative of the acquired pressure signal and integrating the derivative of the acquired pressure signal with the determined trend subtracted. In some embodiments, the subtraction of the determined trend in pressure from the derivative of the acquired pressure signal may comprise a mean subtraction of the determined trend in pressure from the derivative of the acquired pressure signal.

In some embodiments where the trend in pressure is determined, a correction term may be determined based on the determined trend in pressure, for use in compensating the detected artifact due to cuff slippage. For example, a pressure correction term may be determined as the trend in pressure minus an instantaneous pressure, for use in compensating the detected artifact due to cuff slippage in the raw data of the acquired pressure signal. In this way, the resulting pressure signal can be kept constant. The pressure correction term is intended to cancel out the negative step in the raw data of the acquired pressure signal. Similarly, a pressure rate correction term may be determined as the trend in pressure minus an instantaneous pressure rate, for use in compensating the detected artifact due to cuff slippage in the pressure rate signal. In this way, the resulting pressure rate signal can be kept constant. The pressure rate correction term is intended to cancel out the negative impulse in the pressure rate signal.

Thus, in the manner described herein, the artifact due to cuff slippage is compensated. This compensation is performed prior to determining the blood pressure and/or pulse rate of the subject 18. As mentioned previously, the blood pressure and/or pulse rate of the subject 18 is determined by analyzing oscillations in the acquired pressure signal. A person skilled in the art will be aware of the manner in which the blood pressure and/or pulse rate of the subject 18 can be determined by analyzing oscillations in the acquired pressure signal. For example, in some embodiments, the apparatus 12 may be configured to determine the blood pressure of the subject 18 by analyzing the amplitude of the oscillations in the acquired pressure signal (e.g. as described earlier with reference to existing techniques). In some embodiments, the apparatus 12 may be configured to determine the pulse rate of the subject 18 by analyzing the frequency of the oscillations in the acquired pressure signal. For example, the apparatus 12 may be configured to analyze the frequency of the oscillations in the acquired pressure signal by counting the oscillations in the acquired pressure signal, implementing an autocorrelation analysis, implementing a frequency domain analysis, or implementing a more dedicated approach.

In some embodiments, the oscillations in the acquired pressure signal may be detected by passing the acquired pressure signal through an oscillation filter (e.g. a bandpass filter) after the artifact due to cuff slippage is compensated in the manner described herein. As the artifact due to cuff slippage is compensated, the artifact is essentially invisible to the oscillation filter. In this way, the accuracy and thus the reliability of the blood pressure and/or pulse rate of the subject 18 that is determined is improved.

This disclosure also relates to another apparatus for use with a wearable cuff 14 in determining blood pressure and/or pulse rate. As before, with this other apparatus, the wearable cuff 14 is inflatable to pressurize a measurement site 20 of a subject 18. This other apparatus is configured to acquire a pressure signal indicative of pressure in the wearable cuff 14 during inflation of the wearable cuff 14 to pressurize the measurement site 20 of the subject 18 and analyze the acquired pressure signal to detect one or more artifacts due to a pump operable to inflate the wearable cuff 14. This other apparatus is also configured to determine the blood pressure and/or pulse rate of the subject 18 by analyzing oscillations in the acquired pressure signal, wherein determining comprises compensating for the one or more detected artifacts due to the pump. It will be understood that any embodiments described herein involving one or more artifacts due to a pump are applicable to this other apparatus and the apparatus 12 described earlier with reference to FIG. 2, even if not expressly mentioned.

Although not illustrated in FIG. 2, in some embodiments, the apparatus 12 described earlier with reference to FIG. 2 can be further configured to analyze the acquired pressure signal to detect one or more artifacts due to a pump operable to inflate the wearable cuff 14. In some of these embodiments, the determination of the blood pressure and/or pulse rate of the subject can further comprise compensating for the one or more detected artifacts due to the pump. In some embodiments, the apparatus 12 may be configured to compensate for the one or more detected artifacts due to the pump prior to compensating for the artifact due to cuff slippage. An artifact due to a pump operable to inflate the wearable cuff 14 may, for example, comprise a high-frequency disturbance in the pressure of the wearable cuff 14. In embodiments relating to the compensation of artifacts due to cuff slippage, an artifact due to a pump operable to inflate the wearable cuff 14 may comprise a high-frequency disturbance in the pressure of the wearable cuff 14 that interferes with the detection of artifacts due to cuff slippage. In some embodiments involving one or more artifacts due to the pump, the pump can be a diaphragm pump. In the case of a diaphragm pump, for example, an artifact due to such a pump may be related to the passing of the chambers of the diaphragm. In some embodiments, the one or more artifacts due to the pump may comprise one or more artifacts due to a repetitive motion of the pump. The one or more artifacts due to the pump may also be referred to as one or more pump-induced artifacts (or pump-induced oscillations).

In some embodiments involving one or more artifacts due to the pump, the apparatus 12 can be configured to determine (or measure) a rotation speed of a motor of the pump operable to inflate the wearable cuff 14. In some embodiments, the rotation speed of the motor of the pump may be determined from a signal acquired from the pump itself or from one or more sensors on the pump. For example, in some embodiments, the rotation speed of the motor of the pump may be determined from a Hall signal produced due to rotation of the motor, a back electromagnetic flux (BEMF) voltage generated due to rotation of the motor, and/or a supply current provided to the motor. Alternatively or in addition, in other embodiments, the rotation speed of the motor of the pump may be determined from a signal indicative of an angular position of the pump and/or by an analysis of the acquired pressure signal, such as a spectral or correlation analysis (e.g. a frequency analysis) of the acquired pressure signal.

In an embodiment involving a Hall signal, a (e.g. fundamental) frequency of the one or more artifacts due to the pump may be determined, where this frequency is equal to the frequency of rotation of the motor of the pump. Thus, where a Hall signal is produced due to the rotation of the motor, the frequency of the Hall signal can directly relate to the frequency of rotation of the motor of the pump. In some embodiments, the frequency of rotation of the motor of the pump can be determined as 1 divided by the rotation period of the motor of the pump. The rotation period of the motor of the pump can, for example, be determined by counting a duration of a predefined number (e.g. six) of the most recent periods in the Hall signal produced due to the rotation of the motor.

In some embodiments, the frequency of rotation of the motor of the pump may be determined from the acquired pressure signal itself. In some embodiments, the artifact due to the pump can be detected as an identifiable signature at its frequency, e.g. using autocorrelation or frequency analysis, or by counting the number of peaks over a specific period. For example, in some embodiments, the artifact due to the pump may be detected as an optimal frequency (in the case of a frequency analysis) or an optimal time lag (in the case of an autocorrelation analysis). In some embodiments, this detection may be aided by prior knowledge about the pump. For example, the rotation speed of the pump can be predicted based on a voltage applied to the pump, a duty cycle of the pump, and/or a load on the pump (e.g. a baseline pressure on the pump). In some embodiments, a look-up table may be used to predict the frequency of rotation of the pump based on these quantities as a first estimate. In some of these embodiments, the exact rotation frequency can then be determined by searching for the specific frequency in the acquired pressure signal (e.g. using a Fourier or autocorrelation method) based on this first estimate. In some embodiments, the frequency that has the strongest signature in the acquired pressure signal may be searched.

In embodiments where the rotation speed of the motor of the pump is determined, compensating for the one or more detected artifacts due to the pump can be based on the determined rotation speed of the motor of the pump. In some embodiments, compensating for the one or more detected artifacts due to the pump based on the determined rotation speed of the motor of the pump may comprise suppressing one or more harmonics corresponding to the determined rotation speed of the motor of the pump.

In some embodiments, for example, the acquired pressure signal may be filtered (e.g. adaptive filtered) to suppress one or more harmonics corresponding to the determined rotation speed of the motor of the pump. Examples of filters that may be used for this purpose include, but are not limited to, a notch filter (e.g. an adaptive notch filter), a comb filter, or any other filter, or any combination of filters, suitable for suppressing harmonics in a pressure signal. Alternatively or in addition, in some embodiments, compensating for the one or more detected artifacts due to the pump based on the determined rotation speed of the motor of the pump may comprise suppressing one or more signal components corresponding to noise generated by the pump. In some embodiments, for example, the acquired pressure signal may be filtered to suppress one or more signal components corresponding to noise generated by the pump. Examples of filters that may be used for this purpose include, but are not limited to, a prediction filter, or any other filter, or any combination of filters, suitable for suppressing signal components corresponding to noise. In some embodiments, the one or more signal components corresponding to noise generated by the pump may be learned by the apparatus 12.

In an example embodiment, a cascade of infinite impulse response (IIR) notch filters may be configured to compensate for (e.g. cancel) the one or more detected artifacts due to the pump. In more detail, in this example embodiment, the cascade of infinite impulse response (IIR) notch filters may be adapted to the frequency of the one or more detected artifacts due to the pump. Each harmonic h of the artifact frequency $f_n$ can then be cancelled out of the acquired pressure signal by a second-order infinite impulse response (IIR) notch filter. The second-order infinite impulse response (IIR) notch filter may have a transfer function $H_h(z)$ that can be expressed as:

$$H_h(z) = \frac{G - 2G\cos\left(2\pi\frac{hf_n}{f_s}\right)z^{-1} + Gz^{-2}}{1 - 2G\cos\left(2\pi\frac{hf_n}{f_s}\right)z^{-1} + (2G-1)z^{-2}},$$

where $hf_n$ is the harmonic h of the artifact frequency $f_n$, $f_s$ is the sampling frequency (in Hz), z represents the complex frequency, and the parameter G is a gain factor that depends on a 3-dB bandwidth $B_n$ of the infinite impulse response (IIR) notch filter and which can be expressed as $G=1/(1+\tan(\pi B_n/f_s))$. In some embodiments, the 3-dB bandwidth $B_n$ of the infinite impulse response (IIR) notch filter may be in a range from 0.1 Hz to 5 Hz. The resulting filter is a cascade of infinite impulse response (IIR) notch filters at all harmonics of the frequency of the one or more detected artifacts due to the pump. As can be observed from the above equation, only one parameter needs to be adapted at runtime for each notching element. In some embodiments, the cascade of infinite impulse response (IIR) notch filters may be implemented together with an infinite impulse response (IIR) low-pass filter. In some embodiments, only harmonic frequencies lying below a cut-off frequency (e.g. the Nyquist frequency or the maximum signal frequency) may be notched. For example, a switch may be configured to allow only frequencies below the cut-off frequency to pass through the infinite impulse response (IIR) notch filters.

In an alternative example embodiment, a comb filter may be configured to compensate for (e.g. cancel) the one or more detected artifacts due to the pump. In more detail, in this example embodiment, the comb filter may be configured with a delay that is dependent on the rotation speed of the motor of the pump. For example, the comb filter can be a finite impulse response (FIR) filter, which may have a predictable transient behavior in the context of adaptive filtering. In an alternative example embodiment, an identifiable waveform that is specific for the one or more detected artifacts due to the pump may be learned by the apparatus 12 (e.g. using learning filter structures) for the purpose of compensating for the one or more detected artifacts due to the pump. In this example embodiment, the identifiable waveform specific for the one or more detected artifacts due to the pump can then be subtracted from the acquired pressure signal. In an alternative example embodiment, the acquired pressure signal may itself be made less sensitive to oscillations caused by the pump in order to compensate for the one or more detected artifacts due to the pump. For example, in some embodiments, hardware (e.g. a dual-lumen tube) may be positioned to physically separate the at least one pressure sensor from the pump.

In some embodiments, the apparatus 12 may be configured to perform the determination of the rotation speed of the motor of the pump and/or the compensation for the one or more detected artifacts due to the pump in a continuous and/or adaptive process. An example of an adaptive process is where the apparatus 12 is configured to (e.g. continuously) change the frequency of the pressure signal as the rotation speed of the motor of the pump changes. In some embodiments, the apparatus 12 may compensate for the one or more detected artifacts due to the pump using an adaptive filter.

Figure 3A:
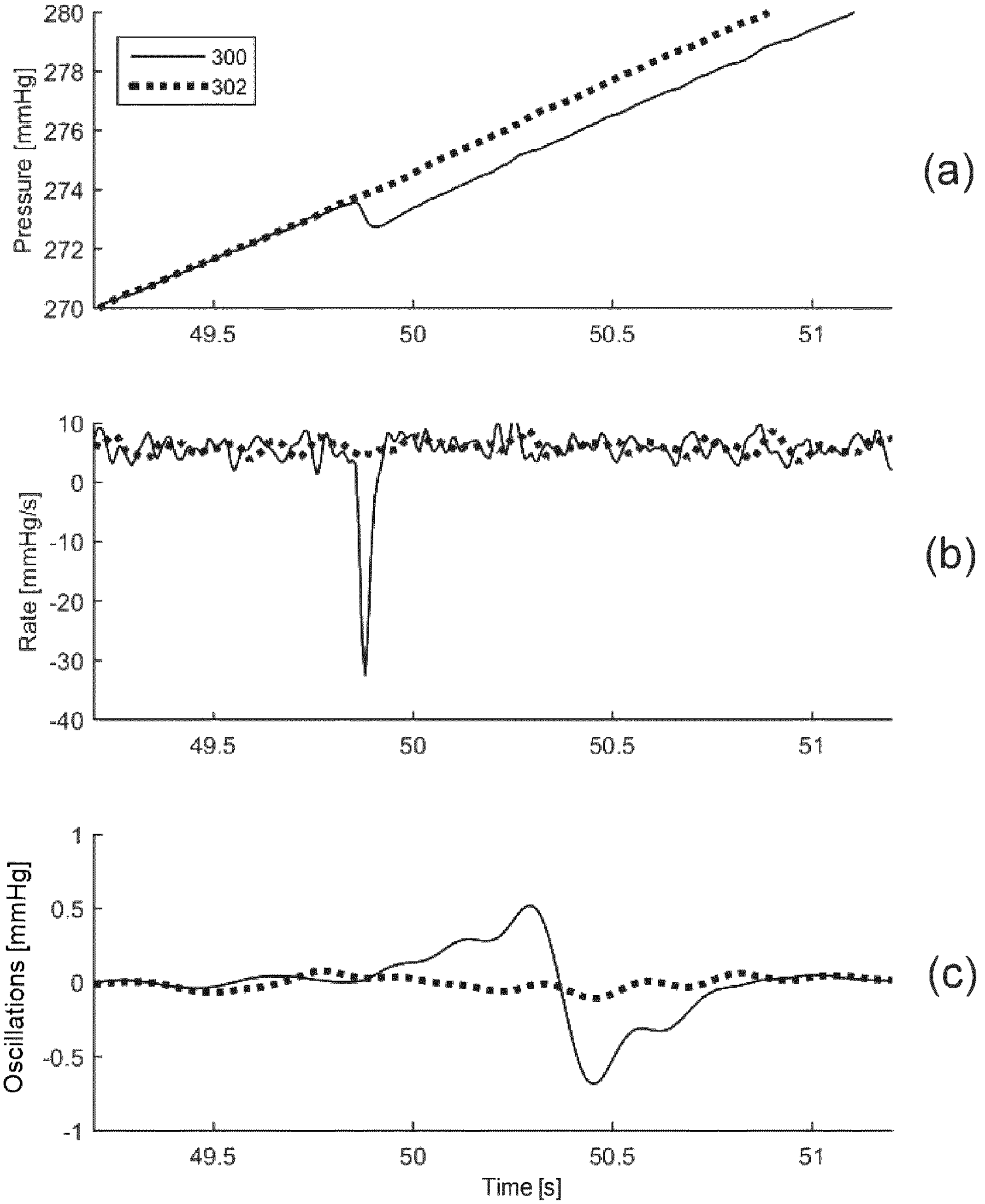
FIG. 3A-B are graphical illustrations of example signals showing artifact compensation according to example embodiments.
Figure 3B:
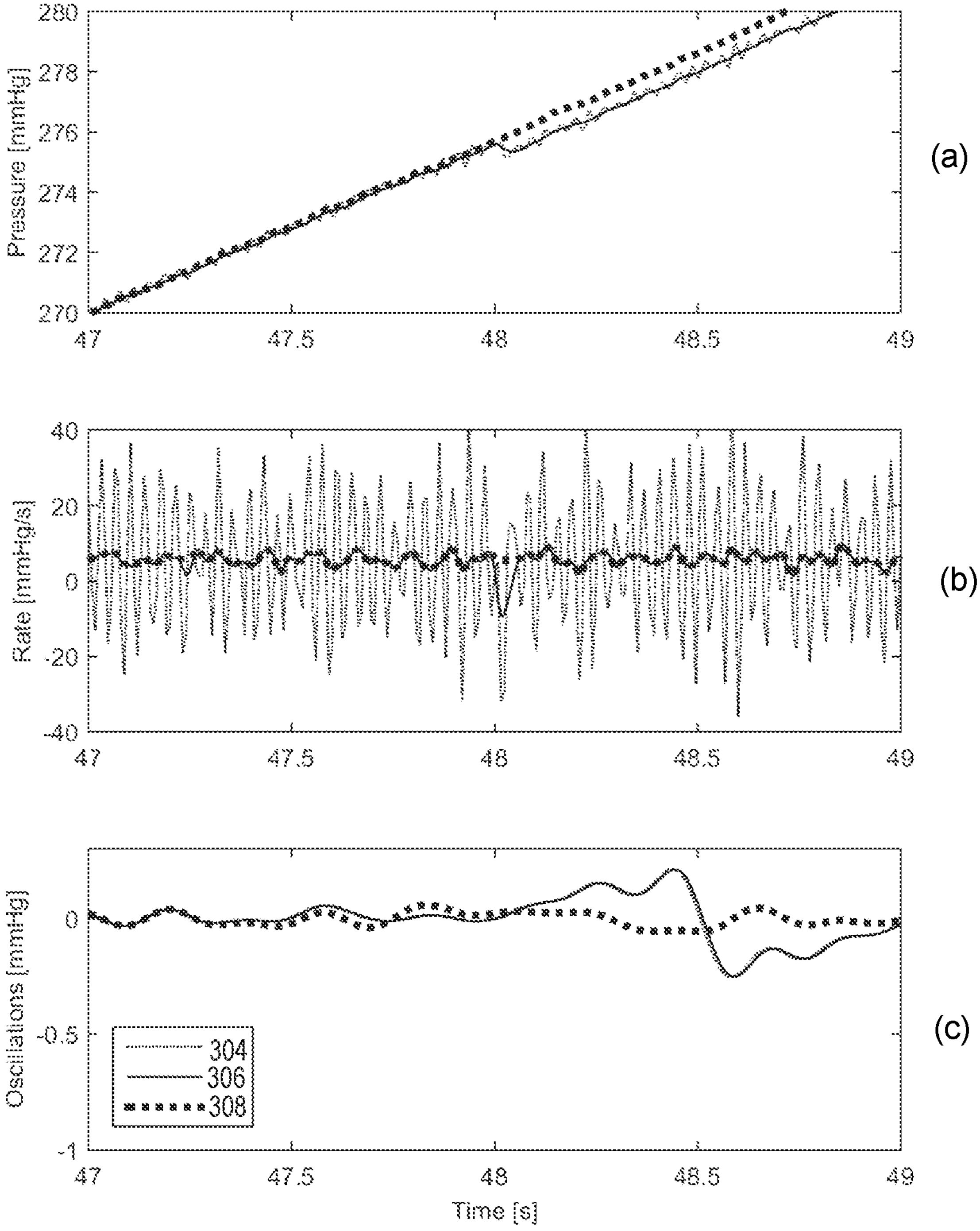

FIG. 3A and FIG. 3B are graphical illustrations of example signals showing artifact compensation according to example embodiments. FIG. 3A(a) and FIG. 3B(a) are graphical illustrations of some example acquired pressure signals on which an artifact due to cuff slippage is superimposed at around 48 seconds. The artifact corresponds to a decrease in pressure during inflation of the wearable cuff 14 due to cuff slippage. As illustrated in FIG. 3A(a) and FIG. 3B(a), this decrease in pressure during inflation of the wearable cuff 14 is in the form of a negative step in the raw data of the acquired pressure signal. FIG. 3A(b) and FIG. 3B(b) are graphical illustrations of the derivative (or, more specifically, the time derivative d/dt) of the acquired pressure signals, i.e. the pressure rate signals. As mentioned earlier, the artifact due to cuff slippage corresponds to a decrease in pressure during inflation of the wearable cuff 14. As illustrated in FIG. 3A(b) and FIG. 3B(b), this decrease in pressure during inflation of the wearable cuff 14 is in the form of a negative impulse in the pressure rate signals. FIG. 3A(c) and FIG. 3B(c) are graphical illustrations of oscillation signals.

In more detail, the signal 300 in FIG. 3A comprises the raw data of the pressure signal in FIG. 3A(a), the derivative of the pressure signal in FIG. 3A(b), and the oscillation signal in FIG. 3A(c) showing the impact of an artifact due to cuff slippage. Also, the signal 302 in FIG. 3B comprises the raw data of the pressure signal in FIG. 3A(a), the derivative of the pressure signal in FIG. 3A(b), and the oscillation signal in FIG. 3A(c) showing the impact of compensating for the detected artifact due to cuff slippage in the manner described herein.

The different signals 304, 306, 308 in FIG. 3B comprise signals showing the impact of artifacts due to both a pump operable to inflate the wearable cuff 14 and due to cuff slippage (labelled as signal 304), signals where the artifacts due to the pump operable to inflate the wearable cuff 14 are suppressed showing the impact of the artifact due to cuff slippage alone (labelled as signal 306), and signals corrected by compensating for the detected artifact due to cuff slippage in the manner described herein (labelled as signal 308).

In FIG. 3B(b), it can be seen from a comparison of the signals 304 and 306 that the artifact due to cuff slippage is even more apparent in the pressure rate signal after compensation of artifacts due to the pump. By focusing on the derivative of the acquired pressure signal (i.e. the pressure rate signal), the artifacts due to the pump are strongly amplified, since a time derivative corresponds to a multiplication with frequency in the Fourier domain. As illustrated in FIG. 3A(c) and FIG. 3B(c), by compensating for the detected artifact due to cuff slippage in the manner described herein, the effect of the artifact due to cuff slippage on the oscillation signal can be significantly reduced. In some embodiments, the effect of an artifact due to cuff slippage on the oscillation signal can be recognized as a step response of a band pass filter (with a minus sign). If the negative impulse in the pressure rate signal (and thus the negative step in the pressure signal) is removed, the effect of the artifact on the oscillation signal can be significantly reduced (e.g. this can be seen from a comparison of the signals 300 and 302 in FIG. 3A(c) and the signals 306 and 308 in FIG. 3B(c)).

Figure 4:
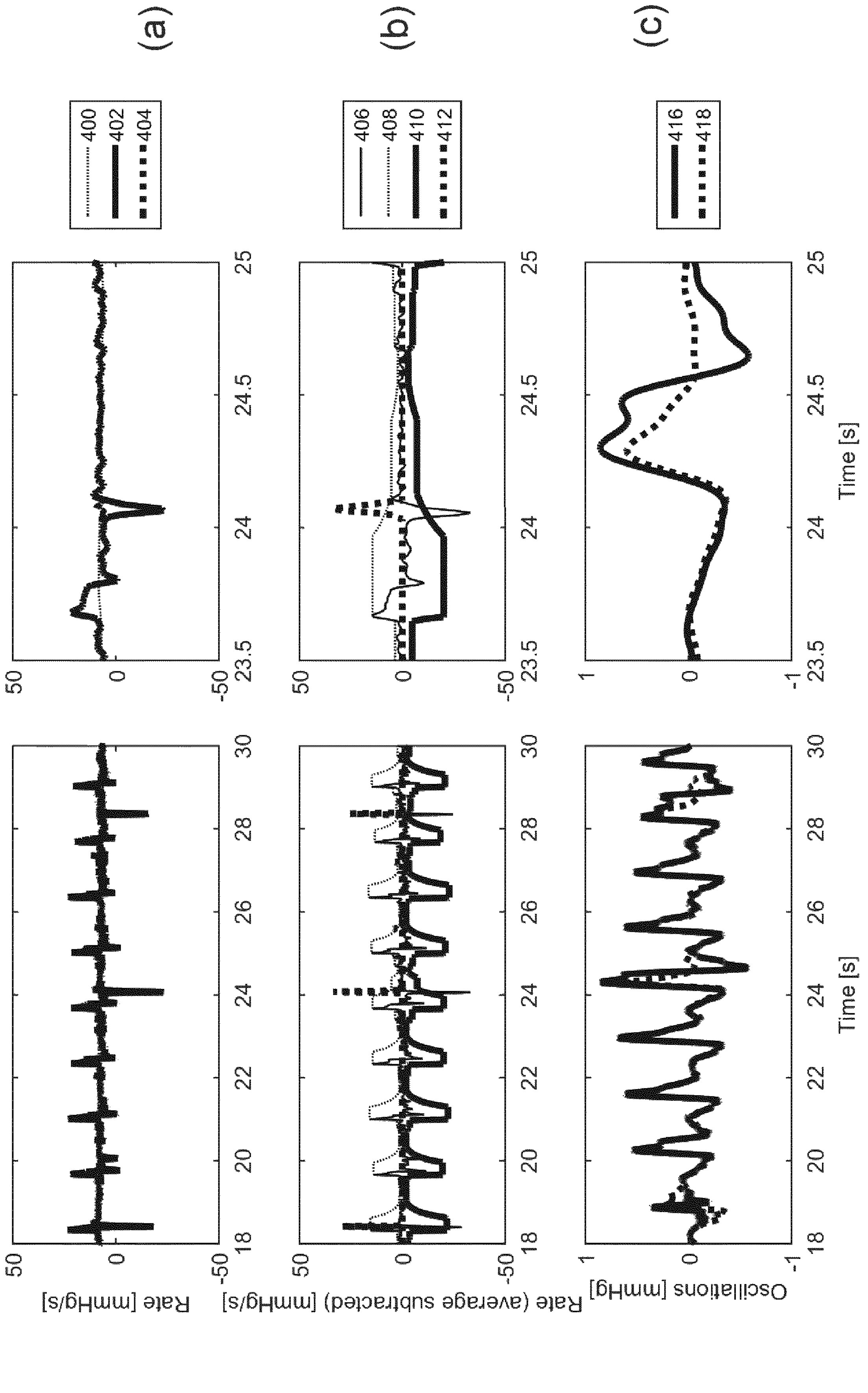
FIG. 4 is a graphical illustration of example signals showing artifact compensation according to another example embodiment.

FIG. 4 is a graphical illustration of example signals showing artifact compensation according to another example embodiment. The same signals that are illustrated on the left of FIG. 4 are zoomed in on the right of FIG. 4. FIG. 4(*a*) is a graphical illustration of a derivative of each of a plurality of example acquired pressure signals, i.e. a plurality of pressure rate signals. More specifically, FIG. 4(*a*) is a graphical illustration of the average of the pressure rate signal (labelled as signal 400), the pressure rate signal itself (labelled as signal 402), and the pressure rate signal after compensation of the detected artifacts due to cuff slippage in the manner described herein (labelled as signal 404). The average of the pressure rate signal (labelled as signal 400) is the determined trend in the acquired pressure signal, as described earlier. FIG. 4(*b*) is a graphical illustration of the pressure rate signal with the average of the pressure rate signal compensated (labelled as signal 406), a running maximum as described earlier (labelled as signal 408), a threshold decrease in pressure rate as described earlier (labelled as signal 410), and a pressure rate correction term as described earlier (labelled as signal 412).

The average of the pressure rate signal may be compensated in the pressure rate signal by subtracting the average of the pressure rate signal from the pressure rate signal, as described earlier. As illustrated in FIG. 4(*b*), the obtained difference signal obtained by this subtraction has a zero mean. In this illustrated example embodiment, the pressure rate correction term is determined in the pressure rate domain. After the pressure rate correction term is determined in the pressure rate domain, the pressure rate correction term can be integrated and added to the raw data of the acquired pressure signal to compensate for the artifact due to cuff slippage in the raw data of the acquired pressure signal.

FIG. 4 (*c*) is a graphical illustration of an oscillation signal. In more detail, FIG. 4(*c*) illustrates the oscillation signal before compensation of the artifact due to cuff slippage (labelled as signal 416) and after compensation of the artifact due to cuff slippage (labelled as signal 418). In this example embodiment, an artifact is detected as a negative impulse at around 24 seconds and 28 seconds in the obtained difference signal. As illustrated in FIG. 4(*c*), by compensating for the detected artifact in the manner described herein, the effect of the artifact on the oscillation signal can be significantly reduced. In this way, corrected oscillations are acquired, which appear to be accurate (judging from their similarity with neighboring oscillations). In this example embodiment, the detected artifact is compensated by applying a correction to the pressure rate signal or, more specifically, by adding the pressure rate correction term to the pressure rate signal. The relatively small negative rate impulse at around 20 seconds may be also be indicative of an artifact. However, the decrease in pressure rate (or, more specifically, the negative rate impulse) is not greater than a threshold decrease in pressure rate and thus the decrease in pressure rate at around 20 seconds is not compensated, e.g. no correction is applied.

Figure 5A:
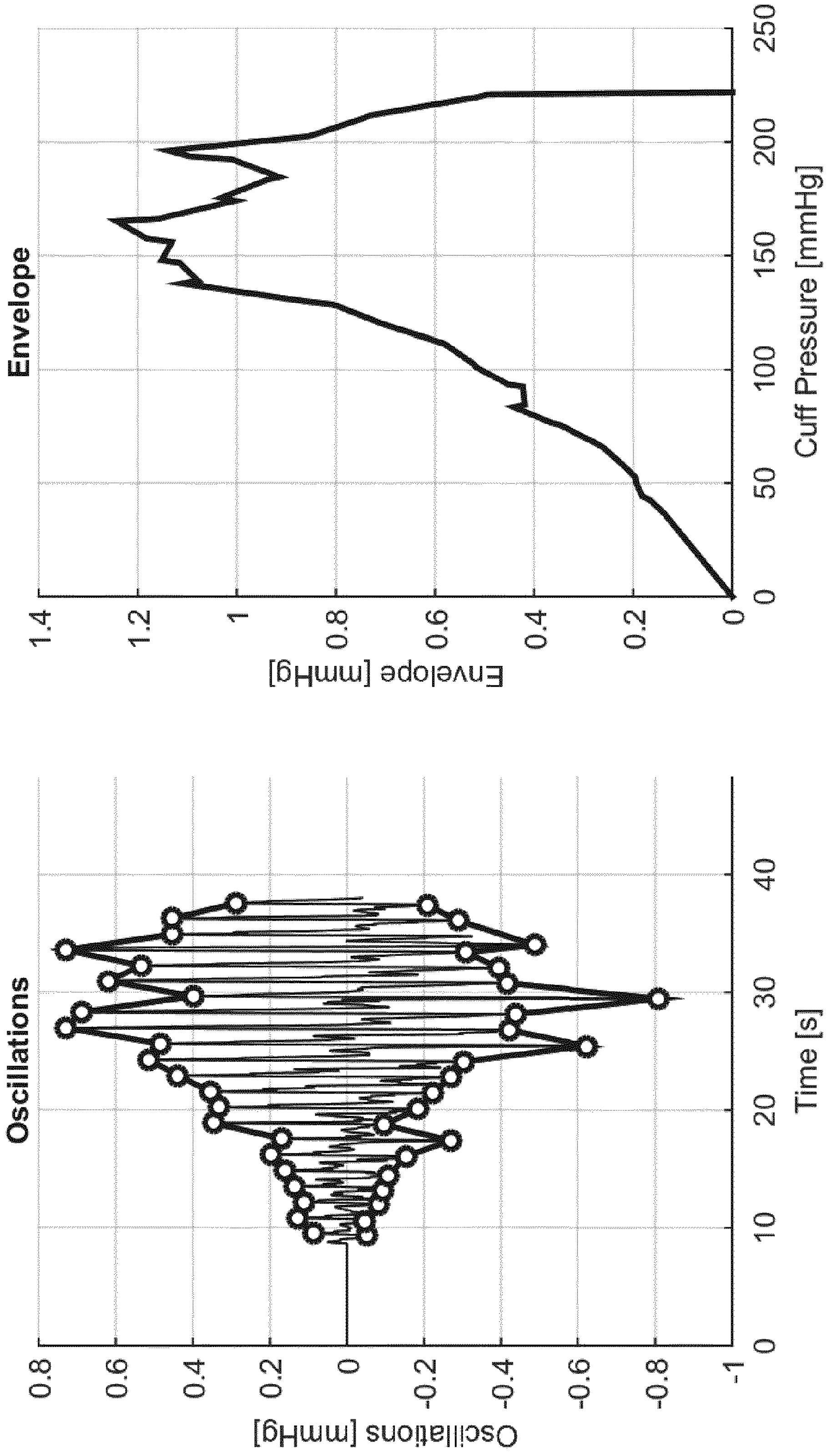
FIG. 5A-B are a graphical illustrations of example signals showing artifact compensation according to another example embodiment.
Figure 5B:
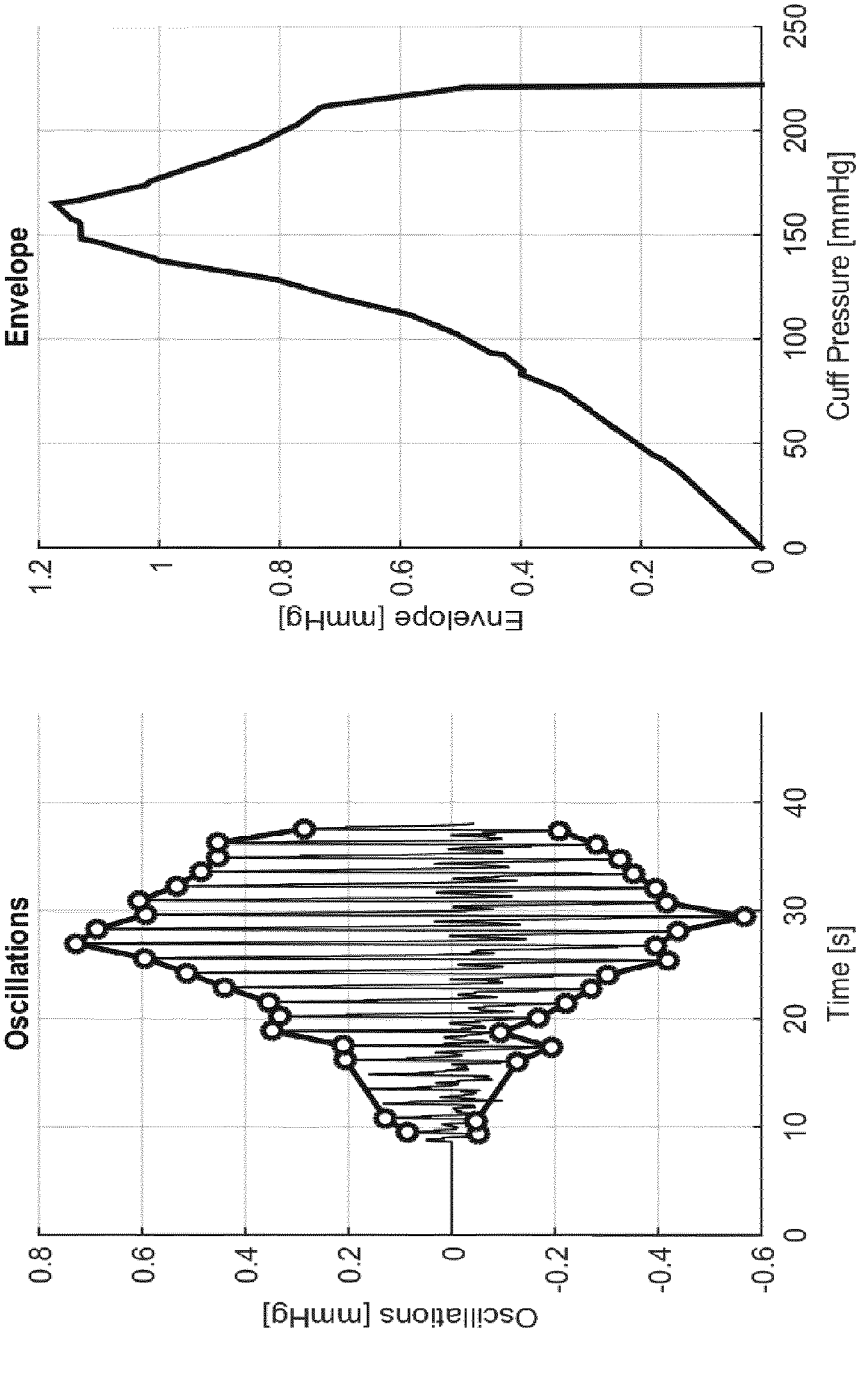

FIG. 5A and FIG. 5B are graphical illustrations of example signals showing artifact compensation according to another example embodiment. FIG. 5A is a graphical illustration of an oscillation signal and an envelope signal where raw data of the acquired pressure signal is processed without compensation of the detected artifacts due to cuff slippage in the manner described herein. FIG. 5B is a graphical illustration of an oscillation signal and an envelope signal where the same raw data of the acquired pressure signal is processed with compensation of the detected artifacts due to cuff slippage in the manner described herein. In each of FIG. 5A and FIG. 5B, the signals are illustrated in pressure oscillations (on the left) and as pressure envelopes (on the right). As can be seen from FIG. 5A and FIG. 5B, the signal envelope is much smoother after compensation of the detected artifacts due to cuff slippage in the manner described herein, allowing for a more robust and reliable determination of blood pressure and/or the pulse rate based on the oscillation envelope.

In any of the embodiments described herein, at least one or all of the steps that the apparatus 12 is configured to perform can be automated. Alternatively or in addition, in any of the embodiments described herein, at least one or all of the steps that the apparatus 12 is configured to perform can be performed in real-time.

There is also provided a computer program product comprising a computer readable medium. The computer readable medium has computer readable code embodied therein. The computer readable code is configured such that, on execution by a suitable computer or processor, the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an apparatus, a method and a computer program product that address the limitations associated with the existing techniques.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for use with a wearable cuff in determining at least one of blood pressure or pulse rate, wherein the wearable cuff is inflatable to pressurize a measurement site of a subject, the apparatus comprising:
- at least one pressure sensor configured to acquire a pressure signal indicative of pressure in the wearable cuff during inflation of the wearable cuff to pressurize the measurement site of the subject; and
- a controller configured to:
- determine a trend in pressure from the acquired pressure signal, wherein the trend in pressure is representative of a baseline pressure;
- remove the determined trend in pressure from the acquired pressure signal;
- detect an artifact from the acquired pressure signal with the determined trend in pressure removed, the artifact occurring at an occasion corresponding to a decrease in pressure during inflation of the wearable cuff due to cuff slippage, wherein detecting the artifact comprises at least one of:
  - detecting a decrease in pressure that is greater than a threshold decrease in pressure; or
  - detecting a decrease in pressure rate that is greater than a threshold decrease in pressure rate;
- compensate for the detected artifact in the acquired pressure signal at the occasion where the detected artifact occurs; and
- determine the at least one of blood pressure or pulse rate of the subject by detecting oscillations in the compensated acquired pressure signal.

2. The apparatus as claimed in claim 1, wherein the apparatus is configured to detect the artifact from the acquired pressure signal by:

analyzing raw data of the acquired pressure signal to detect the artifact.

3. The apparatus as claimed in claim 1, wherein the apparatus is configured to detect the artifact from the acquired pressure signal by:

taking a derivative of the acquired pressure signal; and analyzing the derivative of the acquired pressure signal to detect the artifact.

4. The apparatus as claimed in claim 1, wherein the controller is configured to compensate for the detected artifact by applying a correction to the acquired pressure signal at the occasion where the detected artifact occurs.

5. The apparatus as claimed in claim 4, wherein the controller is configured to apply the correction to the acquired pressure signal by:

subtracting the detected artifact from raw data of the acquired pressure signal at the occasion where the detected artifact occurs to acquire a corrected pressure signal.

6. The apparatus as claimed in claim 4, wherein the controller is configured to apply the correction to the acquired pressure signal by:

subtracting the detected artifact from a derivative of the acquired pressure signal at the occasion where the detected artifact occurs; and integrating the derivative of the acquired pressure signal with the detected artifact subtracted to acquire a corrected pressure signal.

7. The apparatus as claimed in claim 1, wherein any one or more of the threshold decrease in pressure and the threshold decrease in pressure rate is adaptable.

8. The apparatus as claimed in claim 7, wherein the controller is further configured to:

acquire information on amplitude from the acquired pressure signal, wherein any one or more of the threshold decrease in pressure and the threshold rate of pressure decrease is adaptable based on the information acquired on the amplitude.

9. The apparatus as claimed in claim 1, wherein the controller is further configured to:

detect one or more additional artifacts from the acquired pressure signal due to a pump operable to inflate the wearable cuff; and further compensate for the one or more detected artifacts in the acquired pressure signal due to the pump prior to compensating for the artifact due to cuff slippage.

10. The apparatus as claimed in claim 9, wherein the controller is further configured to:

determine a rotation speed of a motor of the pump operable to inflate the wearable cuff; and further compensate for the one or more detected artifacts in the acquired pressure signal due to the pump is based on the determined rotation speed of the motor of the pump.

11. The apparatus as claimed in claim 10, wherein the compensating for the one or more detected artifacts due to the pump based on the determined rotation speed of the motor of the pump comprises:

suppressing one or more harmonics corresponding to the determined rotation speed of the motor of the pump.

12. A wearable cuff suitable for use with the apparatus as claimed in claim 1, said cuff comprising at least one pressure sensor configured for acquiring the pressure signal indicative of the pressure in the wearable cuff during inflation of the wearable cuff.

13. The apparatus as claimed in claim 1, wherein the controller is configured to compensate for the detected artifact by removing from calculations any oscillations in the acquired pressure signal at the occasion where the detected artifact occurs.

14. The apparatus as claimed in claim 1, wherein the controller is configured to detect an artifact using a matched filter applied to raw data of the acquired pressure signal and to a derivative of the acquired pressure signal.

15. The apparatus as claimed in claim 1, wherein the trend in pressure comprises a moving average of the acquired pressure signal over a predefined time period.

16. A method of operating an apparatus for use with a wearable cuff in determining at least one of blood pressure or pulse rate, wherein the wearable cuff is inflatable to pressurize a measurement site of a subject, the method comprising:

acquiring a pressure signal indicative of pressure in the wearable cuff during inflation of the wearable cuff to pressurize the measurement site of the subject;

determining a trend in pressure from the acquired pressure signal, wherein the trend in pressure is representative of a baseline pressure;

removing the determined trend in pressure from the acquired pressure signal;

detecting an artifact from the acquired pressure signal with the determined trend in pressure removed, the artifact occurring at an occasion corresponding to a decrease in pressure during inflation of the wearable cuff due to cuff slippage, wherein detecting the artifact comprises at least one of:

detecting a decrease in pressure that is greater than a threshold decrease in pressure; or detecting a decrease in pressure rate that is greater than a threshold decrease in pressure rate;

compensating for the detected artifact in the acquired pressure signal at the occasion where the detected artifact occurs; and determining the at least one of blood pressure or pulse rate of the subject by detecting oscillations in the compensated acquired pressure signal.

17. The method of claim 16, wherein compensating for the detected artifact comprises:

applying a correction to the acquired pressure signal at the occasion where the detected artifact occurs by subtracting the detected artifact from raw data of the acquired pressure signal at the occasion where the detected artifact occurs to acquire a corrected pressure signal.

18. The method of claim 16, wherein detecting the artifact from the acquired pressure signal comprises:

taking a derivative of the acquired pressure signal; and analyzing the derivative of the acquired pressure signal to detect the artifact.

19. The method of claim 18, wherein compensating for the detected artifact comprises:

applying a correction to the acquired pressure signal at the occasion where the detected artifact occurs by subtracting the detected artifact from the derivative of the acquired pressure signal at the occasion where the detected artifact occurs, and integrating the derivative of the acquired pressure signal with the detected artifact subtracted to acquire a corrected pressure signal.

20. A non-transitory computer readable medium storing computer readable code for use with a wearable cuff in determining at least one of blood pressure or pulse rate, wherein the wearable cuff is inflatable to pressurize a measurement site of a subject, the computer readable code being configured such that, on execution by a computer or processor, causes the computer or processor to:

receive a pressure signal indicative of pressure in the wearable cuff during inflation of the wearable cuff to pressurize the measurement site of the subject;

determine a trend in pressure from the pressure signal, wherein the trend in pressure is representative of a baseline pressure;

remove the determined trend in pressure from the pressure signal;

detect an artifact from the pressure signal with the determined trend in pressure removed, the artifact occurring at an occasion corresponding to a decrease in pressure during inflation of the wearable cuff due to cuff slippage, wherein detecting the artifact comprises at least one of:

detecting a decrease in pressure that is greater than a threshold decrease in pressure; or detecting a decrease in pressure rate that is greater than a threshold decrease in pressure rate; and compensate for the detected artifact in the pressure signal at the occasion where the detected artifact occurs; and determine the at least one of blood pressure or pulse rate of the subject by detecting oscillations in the compensated pressure signal.

* * * * *